United States Patent [19]

Butera et al.

[11] Patent Number: 5,532,245
[45] Date of Patent: Jul. 2, 1996

[54] SUBSTITUTED N-HETEROARYL-1,2-DIAMINOCYCLOBUTENE-3,4-DIONE COMPOUNDS

[75] Inventors: John A. Butera, Clarksburg; Schuyler A. Antane, Lawrenceville; Bradford H. Hirth, Monmouth Junction, all of N.J.

[73] Assignee: American Home Products Corporation, Madison, N.J.

[21] Appl. No.: 477,840

[22] Filed: Jun. 7, 1995

Related U.S. Application Data

[62] Division of Ser. No. 334,475, Nov. 4, 1994, Pat. No. 5,466,712.

[51] Int. Cl.⁶ .................... C07D 213/02; C07D 239/24; A61K 31/44; A61K 31/505
[52] U.S. Cl. .......... 514/272; 514/341; 514/352; 544/331; 544/332; 546/312; 546/272.7; 546/310; 546/307; 546/308; 546/309; 546/287; 546/289; 546/291; 546/293; 546/294; 546/297
[58] Field of Search .................. 546/278, 312; 544/331, 332; 514/341, 352, 272

[56] References Cited

U.S. PATENT DOCUMENTS

| | | | |
|---|---|---|---|
| 4,390,701 | 6/1983 | Algieri et al. | 546/334 |
| 4,673,747 | 6/1987 | Nohara et al. | 546/235 |

FOREIGN PATENT DOCUMENTS

| | | | |
|---|---|---|---|
| 0426379 | 5/1991 | European Pat. Off. | 548/338.1 |
| 6092915 | 4/1994 | Japan | 546/334 |

OTHER PUBLICATIONS

Tietze, et al., Squaric Acid Diethyl Ester: A New Coupling Reagent for the Formation of Drug Biopolymer Conjugates. Synthesis of Squaric Acid Ester Amides and Diamides, Chem. Ber., 124, p. 1215, 1991.

Tietze, et al., Conjugation of p–Aminophenyl Glycosides with Squaric Acid Diester to a Carrier Protein and the Use of Neoglycoprotein in the Histochemical Detection of Lectins, Bioconjugate Chem., 2, p. 148, 1991.

Ehrhardt, et al., Amide und Thioamide der Quadratsaure: Synthese und Reaktionen, Chem. Ber., 110, p. 2506, 1977.

Neuse, et al., Amidierung von Quadratsaure–estern, Liebigs Ann. Chem., p. 619, 1973.

Primary Examiner—Zinna Northington Davis
Attorney, Agent, or Firm—Richard K. Jackson

[57] ABSTRACT

The compounds of the formula:

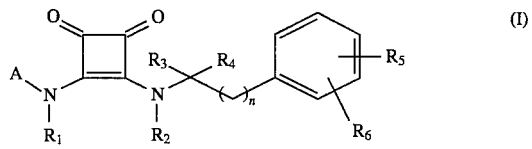

wherein $R_1$ is hydrogen, straight or branched chain alkyl, cyclic or bicyclic alkyl, alkanoyl, alkylsulfonyl, aroyl, arylalkenoyl, arylsulfonyl, arylalkanoyl or arylalkylsulfonyl; $R_2$ is hydrogen, straight or branched chain alkyl or cyclic or bicyclic alkyl; A is selected from the following:

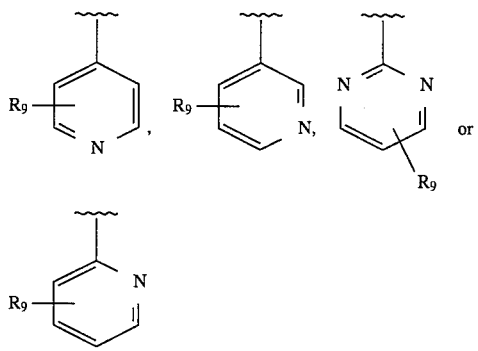

wherein $R_9$ is hydrogen, alkyl, perfluoroalkyl, alkoxy, perfluoroalkoxy, amino, mono- or dialkylamino, alkylsulfonamido, alkylcarboxamido, nitro, cyano, carboxyl, chloro, bromo, fluoro or iodo; n is an integer from 0 to 6; $R_3$ and $R_4$, independent from each other, are hydrogen, straight or branched chain alkyl, cyclic or bicyclic alkyl, perfluoroalkyl, hydroxyalkyl, alkoxyalkyl, fluoro, or, when taken together, form a spirocyclic ring; $R_5$ and $R_6$, independent from each other, are selected from the following: cyano, nitro, amino, alkyl, perfluoroalkyl, alkoxy, perfluoroalkoxy, mono- or dialkylamino, sulfonamide, alkylsulfonamido, arylsulfonamido, alkylcarboxamido, arylcarboxamido, alkylsulfonyl, perfluoroalkylsulfonyl, arylsulfonyl, chloro, bromo, fluoro, iodo, 1-imidazolyl, carboxyl, carboalkoxy, hydroxyl, or hydrogen; and the pharmaceutically acceptable salts thereof relax smooth muscles.

7 Claims, No Drawings

SUBSTITUTED N-HETEROARYL-1,2-DIAMINOCYCLOBUTENE-3,4-DIONE COMPOUNDS

This is a Division of application Ser. No. 08/334,475 filed Nov. 4, 1994 now U.S. Pat. No. 5,466,712 issued Nov. 14, 1995.

BACKGROUND OF INVENTION

The present invention relates to novel 1, 2-diamino derivatives of cyclobutene 3-4-diones having pharmacological activity, to a process for their preparation, to pharmaceutical compositions containing them, and to their use in the treatment of disorders associated with smooth muscle contraction; via potassium channel modulation. Such disorders include, but are not limited to: urinary incontinence, hypertension, asthma, premature labor, irritable bowel syndrome, congestive heart failure, angina, and cerebral vascular disease.

Stemp et al. disclose a class of amino substituted cyclobutenedione derivatives of chromans described as having blood pressure lowering activity and bronchodilatory activity in EP-426379-A2. Several series of 1-amino-2-phenylalkylamino-cyclobutene- 3,4-diones are reported as H-2 receptor antagonists by Algieri et al. in U.S. Pat. No. 4,390,701 and its numerous divisionals and CIPs. Several related 1-amino-2-phenoxyalkylamino derivatives are disclosed by Nohara et al. in U.S. Pat. No. 4,673,747.

The syntheses of representative 1,2-diamino-cyclobutene-3,4-diones are described in the following publications: Tietze et al., *Chem Ber.* 1991, 124, 1215; Tietze et al., *Bioconjugate Chem.* 1991, 2, 148; Ehrhardt et al., *Chem. Ber.* 1977, 110, 2506, and Neuse et al., *Liebigs Ann. Chem.* 1973, 619.

DESCRIPTION OF THE INVENTION

Accordingly, the present invention discloses compounds represented by the formula (I):

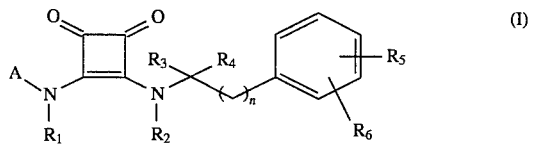

wherein:

$R_1$ is hydrogen, $C_{1-10}$ straight or branched chain alkyl, $C_{3-10}$ cyclic or bicyclic alkyl, alkanoyl of 2 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

$R_2$ is hydrogen, $C_{1-10}$ straight or branched chain alkyl or $C_{3-10}$ cyclic or bicyclic alkyl;

A is a substituted phenyl group of the following formula:

wherein:

$R_7$ and $R_8$, independent from each other, are selected from the following: cyano, nitro, amino, $C_{1-6}$ alkyl, $C_{1-6}$ perfluoroalkyl, $C_{1-6}$ alkoxy, $C_{1-6}$ perfluoroalkoxy, amino, $C_{1-12}$ mono- or dialkylamino, sulfonamide, $C_{1-6}$ alkylsulfonamido, $C_{6-12}$ arylsulfonamido, $C_{1-6}$ alkylcarboxamido, $C_{6-12}$ arylcarboxamido, $C_{1-6}$ alkylsulfonyl, $C_{1-6}$ perfluoroalkylsulfonyl, $C_{6-12}$ arylsulfonyl, chloro, bromo, fluoro, iodo, 1-imidazolyl, carboxyl, carboalkoxy of 2 to 7 carbon atoms, hydroxyl or hydrogen;

or, A is Het where Het is selected from the following:

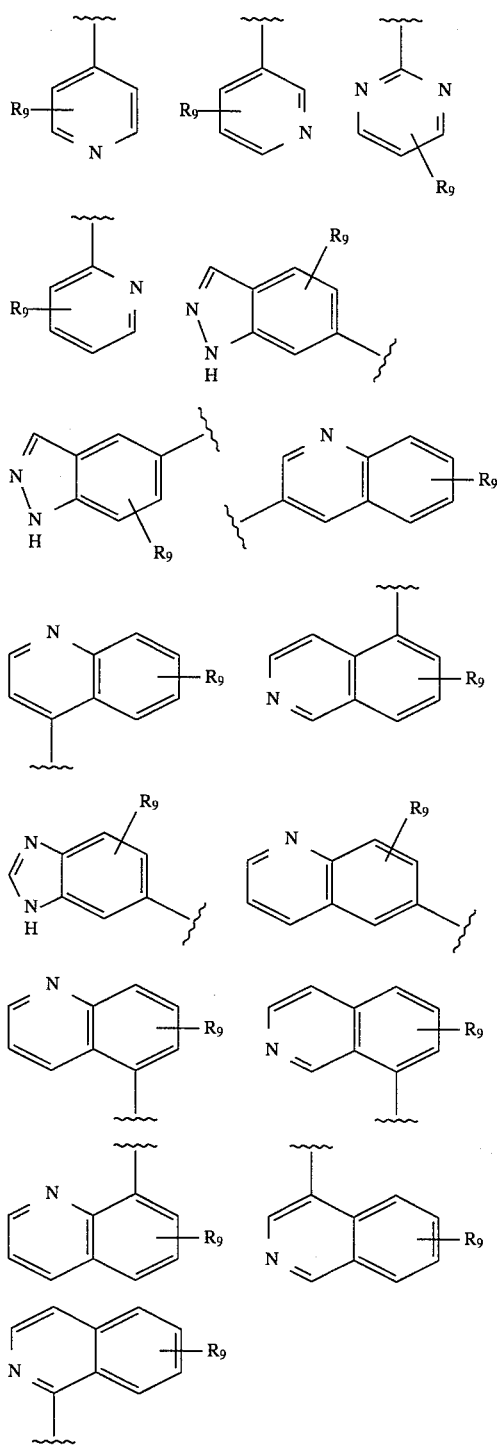

wherein:

$R_9$ is hydrogen, $C_{1-6}$ alkyl, $C_{1-6}$ perfluoroalkyl, $C_{1-6}$ alkoxy, $C_{1-6}$ perfluoroalkoxy, amino, $C_{1-12}$ mono- or dialkylamino. $C_{1-6}$ alkylsulfonamido, $C_{1-6}$ alkylcarboxamido, nitro, cyano, carboxyl, chloro, bromo, fluoro, iodo;

n is an integer from 0 to 6;

$R_3$ and $R_4$ are, independent from each other, hydrogen, $C_{1-10}$ straight or branched chain alkyl, or $C_{3-10}$ cyclic or bicyclic alkyl; $C_{1-10}$ perfluoro alkyl, $C_{1-10}$ hydroxyalkyl, $C_{1-10}$ alkoxyalkyl, fluoro; or, when taken together, form a spirocyclic ring containing a total of 3–7 carbon atoms;

$R_5$ and $R_6$, independent from each other, are selected from the following: cyano, nitro, amino, $C_{1-6}$ alkyl, $C_{1-6}$ perfluoroalkyl, $C_{1-6}$ alkoxy, $C_{1-6}$ perfluoroalkoxy, amino, $C_{1-12}$ mono- or dialkylamino, sulfonamide, $C_{1-6}$ alkylsulfonamido, $C_{6-12}$ arylsulfonamido, $C_{1-6}$ alkylcarboxamido, $C_{6-12}$ arylcarboxamido, $C_{1-6}$ alkylsulfonyl, $C_{1-6}$ perfluoroalkylsulfonyl, $C_{6-12}$ arylsulfonyl, chloro, bromo, fluoro, iodo, 1-imidazolyl, carboxyl, carboalkoxy, hydroxyl, or hydrogen;

or a pharmaceutically acceptable salt thereof.

A preferred aspect of this invention includes compounds of formula (I) wherein:

$R_1$ and $R_2$ are as stated above;

A is a substituted phenyl group of the following formula:

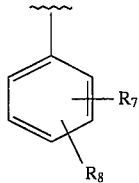

wherein:

$R_7$ and $R_8$, independent from each other, are selected from the following: cyano, nitro, amino, chloro, bromo, fluoro, iodo, 1-imidazolyl, carboxyl, hydrogen;

or A is Het where Het is selected from the following:

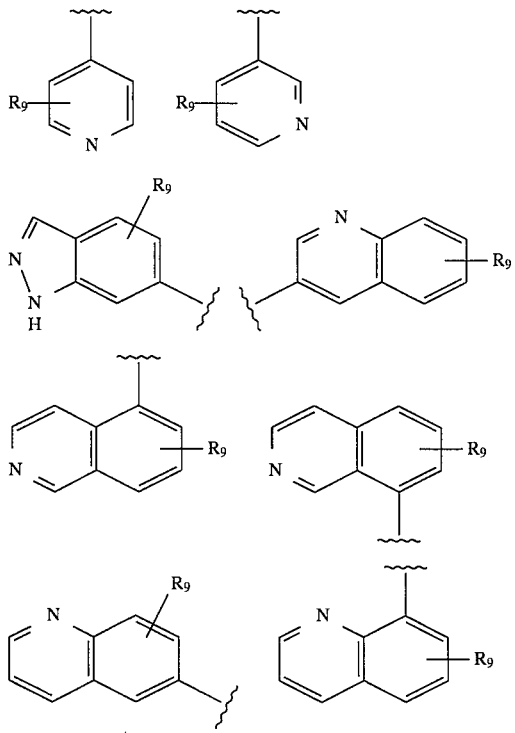

wherein:

$R_9$ is as stated above;

n=0;

$R_3$ and $R_4$ are, independent from each other, hydrogen, $C_{1-10}$ straight or branched chain alkyl, $C_{1-10}$ perfluoro alkyl, $C_{1-10}$ hydroxyalkyl or fluoro;

$R_5$ and $R_6$, independent from each other, are selected from the following: cyano, nitro, amino, $C_{1-6}$ alkyl, $C_{1-6}$ perfluoroalkyl, $C_{1-6}$ alkoxy, $C_{1-6}$ perfluoroalkoxy, amino, chloro, bromo, fluoro, iodo, carboxyl, carboalkoxy, hydroxyl, hydrogen;

or a pharmaceutically acceptable salt thereof.

It is understood that the definition of the compounds of formula (I), when $R_1$, $R_2$, $R_3$, $R_4$, $R_5$, or $R_6$ contain asymmetric carbons, or when $R_3$ is different from $R_4$, encompass all possible stereoisomers and mixtures thereof. In particular, it encompasses racemic modifications and optical isomers. The optical isomers may be obtained in pure form by standard separation techniques. The pharmaceutically acceptable salts are those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids. Where $R_3$, $R_4$, $R_5$ or $R_6$ are carboxyl groups, salts of the compounds of this invention may be formed with bases such as alkali metals (Na, K, Li) or the alkaline earth metals (Ca or Mg).

The acyl groups representing $R_1$ are derived from such acids as acetic, propionic, butyric, valeric, caproic, methanesulfonic-ethanesulfonic, benzoic, toluic, cinnamic, phenylsulfonic, phenylacetic, naphthylacetic, benzylsulfonic and the like.

The present invention also provides a process for the preparation of a compound of formula (I). More particularly, the compounds of formula (I) may be prepared by reacting a compound of formula (II):

wherein X is defined as a suitably designed leaving group such as methoxy, ethoxy, isopropoxy, halogeno, or similar groups, with a compound of formula (III):

wherein $A_1$ is A, and $Ra_1$ is $R_1$, as defined hereinbefore or a group of atoms convertible thereto, followed by treatment with a compound of formula (IV):

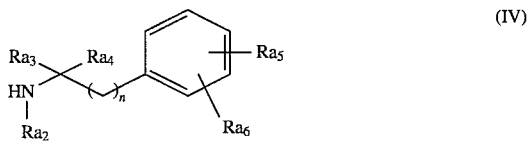

wherein n is as described above and $Ra_2$, $Ra_3$, $Ra_4$, $Ra_5$, $Ra_6$ are $R_2$, $R_3$, $R_4$, $R_5$, $R_6$, respectively, as defined hereinbefore or a group of atoms convertible thereto, in a solvent such as ethanol or methanol at elevated temperatures.

As mentioned previously, the compounds of formula (I) have been found to relax smooth muscle. They are therefore useful in the treatment of disorders associated with smooth muscle contraction, disorders involving excessive smooth muscle contraction of the urinary tract (such as incontinence), or of the gastrointestinal tract (such as irritable bowel syndrome), asthma, and hair loss. Furthermore, the compounds of formula (I) are active as potassium channel activators which render them useful for treatment of peripheral vascular disease, congestive heart failure, stroke, anxiety, cerebral anoxia and other neurodegenerative disorders.

The present invention accordingly provides a pharmaceutical composition which comprises a compound of this invention and a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration, it is preferred that composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

The present invention further provides a compound of the invention for use as an active therapeutic substance. Compounds of formula (I) are of particular use in inducing smooth muscle relaxation.

The present invention further provides a method of treating smooth muscle disorders in mammals including man, which comprises administering to the afflicted mammal an effective amount of a compound or a pharmaceutical composition of the invention.

The following examples are presented to illustrate rather than limit the methods for production of representative compounds of the invention.

EXAMPLE 1

4-[3,4-Dioxo-2-((R)-1-Phenyl-Ethylamino)-Cyclobut-1-Enylamino]-Benzonitrile

Step 1)

Preparation of 4-(3,4-Dioxo-2-ethoxy-cyclobut-1-enylamino)-benzonitrile

4-Aminobenzonitrile (3.47 g, 29.4 mmol) was added to a solution of 3,4-diethyoxy- 3-cyclobutene-1,2-dione (5.00 g, 29.4 mmol) in absolute ethanol (100 mL). The mixture was heated at reflux overnight. The mixture was cooled, and the resulting yellow precipitate was collected by vacuum filtration. Yield: 2.60 g (37%): mp 218°–222° C.; $^1$H NMR (DMSO-$d_6$): δ11.07 (s, 1H), 7.81 (d, 2H), 7.56 (d, 2H), 4.79 (q, 2H), 1.46 (t, 3H).

Step 2)

Preparation of 4-[3,4-dioxo-2-((R)- 1-phenyl-ethylamino)-cyclobut- 1-enylamino]-benzonitrile To the above squarate (0.50 g, 2.06 mmol) in ethanol (10 mL) was added (R)-α -methylbenzylamine (0.27 mL, 2.1 mmol). The mixture was heated at reflux for 16 hours and vacuum filtered. The precipitate was recrystallized from methanol to afford 0.17 g (26%) of product as a pale yellow solid: mp 273°–274° C.; $[α]^{25}_D$–53.20 (DMSO); $^1$H NMR (DMSO-$d_6$): δ 9.91 (s, 1H), 8.2 L(d, 1H), 7.72 (d, 1H), 7.79–7.31 (m, 9H), 5.29 (m, 1H), 1.59 (d, 3H). IR (KBr): 3200, 2230, 1790, 1670, 1600 cm$^{-1}$; MS (m/z) 317 (M$^+$).

Elemental analysis for $C_{19}H_{15}N_3O_2$ Calc'd: C, 71.91; H, 4.76; N, 13.24. Found: C, 71.26; H, 4.86; N, 13.49.

EXAMPLE 2

3-(5-Bromo-Pyridin-3-Ylamino)-4-((R)-1-Phenyl-Ethylamino)-Cyclobut- 3-Ene-1,2-Dione Step 1)

Preparation of 3-(5-bromo-pyridin-3-ylamino)-4-ethoxycyclobut- 3-ene-1,2-dione)

3-Amino-5-bromopyridine (1.92 g, 11.3 mmol) was added to a solution of 3,4-diethoxy-3-cyclobutene-1,2-dione (2.24 g, 11.1 mmol) in absolute ethanol (30 mL). The mixture was heated at reflux for 18 hours, cooled and filtered. The filtrate was concentrated and the resulting residue chromatographed ($CH_3OH/CH_2Cl_2$) to afford 2.06 g (62%) of product as an off-white solid: $^1$H NMR (DMSO-$d_6$): δ 11.00 (s, 1H), 8.56 (s, 1H), 8.42 (s, 1H), 8.09 (s, 1H), 4.79 (q, 2H), 1.42 (t, 3H).

Step 2)

Preparation of 3-(5-Bromo-pyridin-3-ylamino)-4-((R)-1-phenyl-ethylamino)-cyclobut- 3-ene-1,2-dione To the above squarate (0.815 g, 2.74 mmol) in ethanol (25 mL) was added (R)-α-methylbenzylamine (0.36 mL, 2.8 mmol). The mixture was heated at reflux for 23 hours. The precipitate was filtered off and rinsed with ethanol to afford 0.92 g (90%) of product as an off-white solid: mp 268°–271° C. (dec); $[α]^{25}_D$+6.57 (DMSO); $^1$H NMR (DMSO-$d_6$): δ 9.85 (s, 1H), 8.44–8.15 (m, 4H), 7.43–7.27 (m, 5H), 5.29 (m, 1H), 1.59 (d, 3H). IR (KBr): 3200, 1790, 1670, 1590 cm$^-$; MS (m/z) 372 (MH$^+$).

Elemental analysis for $C_{17}H_{14}BrN_3O_2$ Calc'd: C, 54.86; H, 3.79; N, 11.29. Found: C, 54.88; H, 3.67; N, 11.20.

EXAMPLE 3

3-( 2-Methoxy-5-Trifluoromethyl-Phenylamino)-4-((R)-1-Phenyl-Ethylamino)-Cyclobut- 3-Ene-1.2-Dione Step 1)

Preparation of 3-ethoxy-4-(2-methoxy-5-trifluoromethylphenylamino)-cyclobut- 3-ene-1,2-dione 2-Methoxy-5-trifluoromethylaniline (5.62 g, 29.4 mmol) was added to a solution of 3,4-diethoxy-3-cyclobutene-1,2-dione (5.00 g, 29.4 mmol) in absolute ethanol (100 mL). The mixture was heated at reflux for 66 hour, cooled and filtered. The precipitate was purified by chromatography ($CH_3OH/CH_2Cl_2$) to afford 1.88 g (20%) of product as a yellow solid: $^1$H NMR (DMSO-$d_6$): δ 10.42 (s, 1H), 7.64–7.20 (m, 3H), 4.69 (q, 2H), 3.90 (s, 3H), 1.34 (t, 3H).

Step 2) Preparation of 3-(2-methoxy-5-trifluoromethylphenylamino)-4-((R)- 1-phenyl-ethylamine)-cyclobut-3-ene-1,2-dione To the above squarate (0.806 g, 2.56 mmol) in ethanol (10 mL) was added (R)-α-methylbenzylamine (0.33 mL, 2.6 mmol). The mixture was heated at reflux for 23 hours. The clear yellow solution was concentrated and the resulting foam purified by chromatography ($CH_3OH/CH_2Cl_2$)to afford 0.84 g (84%) of product as a white solid: mp 115°–124° C.; $[α]^{25}_D$–33.61 (DMSO); $^1$H NMR (DMSO-$d_6$): a 9.37 (s, 1H), 8.72 (d, 1H), 8.24 (s, 1H), 7.42–7.19 (m, 7H), 5.33 (m, 1H), 3.97 (s, 1H), 1.59 (d, 3H). IR (KBr): 3250, 1790, 1690, 1610 cm$^{-1}$; MS (m/z) 391 (MH$^+$).

Elemental analysis for $C_{20}H_{17}F_3N_2O_3$ Calc'd: C, 61.54; H, 4.39; N, 7.18. Found: C, 61.42; H, 4.26; N, 7.23.

EXAMPLE 4

3-((R)-1-Phenyl-Ethylamino)-4-(Pyridin-4-Ylamino)-Cyclobut-3-ene-1,2-Dione

Step 1)

Preparation of 3-ethoxy-4-(pyridin-4-ylamino)-cyclobut-3-ene- 1,2-dione

To a solution of 3,4-diethoxy-3-cyclobutene-1,2-dione (5.00 g, 29.4 mmol) in ethanol (100 mL) was added a suspension of 4-aminopyridine (2.77 g, 29.4 mmol) in ethanol (50 mL). The reaction mixture was heated at reflux for 4 hours. Concentration and chromatography (EtOAc) of the resulting residue afforded 0.632 g (10%) of product as a white solid: $^1$H NMR (DMSO-d$_6$): δ 11.18 (br s, 1H), 8.45 (d, 2H), 7.40 (d, 2H), 4.80 (q, 2H), 1.43 (t, 3H).

Step 2) Preparation of 3-((R)-1-phenyl-ethylamino)-4-(pyridin-4-ylamino)-cyclobut- 3-ene-1,2-dione To the above squarate (0.850 g, 3.90 mmol) in ethanol (25 mL) was added (R)-α-methylbenzylamine (0.51 mL, 4.0 mmol). The mixture was heated at reflux for 23 hours. The precipitate was filtered off and rinsed with ethanol. Chromatography (CH$_3$OH/CH$_2$Cl$_2$) afforded 0.276 g (24%) of product as an off-white solid: mp 252°–254° C. (dec); [α]$^{25}_D$–31.45 (DMSO); $^1$H NMR (DMSO-d$_6$): δ 9.82 (s, 1H), 8.40 (d, 2H), 8.22 (d, 1H), 7.45–7.38 (m, 7H), 5.28 (m, 1H), 1.59 (d, 3H). IR (KBr): 3200, 1800, 1675, 1590 cm$^{-1}$; MS (m/z) 293 (MH$^+$).

Elemental analysis for $C_{17}H_{15}N_3O_2$ Calc'd: C, 69.61; H, 5.15; N, 14.33. Found: C, 69.49; H, 5.06; N, 14.18.

EXAMPLE 5

4-[3,4-Dioxo-2-((S)-1-Phenyl-Ethylamino)-Cyclobut-1-Enylamino]-Benzonitrile

To the squarate of Example 1, step 1 (0.50 g, 2.06 mmol) in ethanol (10 mL) was added (S)-α-methylbenzylamine (0.27 mL, 2.1 mmol). The mixture was heated at reflux for 16 hours and vacuum filtered. The precipitate was recrystallized from methanol to afford 0.17 g (26%) of product as a pale yellow solid: mp 269°–270° C.; [α]$^{25}_D$+46.47 (DMSO); $^1$H NMR (DMSO-d$_6$): δ 9.91 (s, 1H), 8.21 (d, 1H), 7.72 (d, 1H), 7.79–7.31 (m, 9H), 5.29 (m, 1H), 1.59 (d, 3H). IR (KBr): 3200, 2230, 1790, 1670, 1600 cm$^{-1}$; MS (m/z) 317 (M$^+$). Elemental analysis for $C_{19}H_{15}N_3O_2$ Calc'd: C, 71.91; H, 4.76; N, 13.24. Found: C, 71.17; H, 4.83; N, 13.34.

EXAMPLE 6

3-(4-Trifluoromethoxy-Phenylamino)-4-((R)(–)-1-Phenyl-Ethylamino)-Cyclobut- 3-Ene-1,2-Dione Step 1)

Preparation of 3-ethoxy-4-(4-trifluoromethoxy-phenylamino)-cyclobut- 3-ene-1,2-dione 4-Trifluoromethoxyaniline (5.00 g, 28.2 mmol) was added to a solution of 3,4-diethoxy-3-cyclobutene-1,2-dione (5.00 g, 29.4 mmol) in absolute ethanol (50 mL). The mixture was heated at reflux overnight, then vacuum filtered hot. The filtrate was reduced in volume and the resulting precipitate was filtered to afford 4.50 g (53%) of white solid: mp 145°–146° C.; $^1$H NMR (DMSO-d$_6$): δ 10.87 (s, 1H), 7.45 (d, 2H), 7.36 (d, 2H), 4.75 (q, 2H), 1.41 (t, 3H).

Step 2)

Preparation of 3-(4-trifluoromethoxy-phenylamino)-4-((R)- 1-phenyl-ethylamine)-cyclobut-3-ene-1,2-dione To the above squarate (0.330 g, 1.10 mmol) in ethanol (25 mL) was added (R)-α-methylbenzylamine (0.135 mg, 1.11 mmol). The reaction was refluxed for 23 hours. Upon cooling, the product precipitated as a white solid 0.350 g (84%): mp 258°–260° C.; [α]$^{25}_D$–17.52 (DMSO); $^1$H NMR (DMSO-d$_6$): δ 9.70 (s, 1H), 8.12 (d, 1H), 7.51–7.28 (m, 9H), 5.28 (m, 1H), 1.59 (d, 3H). IR (KBr): 3250, 1800, 1675, 1600 cm$^{-1}$; MS (m/z) 377 (MH$^+$).

Elemental analysis for $C_{19}H_{15}F_3N_2O_3$ Calc'd: C, 60.64; H, 4.02; N, 7.44. Found: C, 60.40; H, 4.01; N, 7.21.

EXAMPLE 7

(R)-4-{2-[1-(4-Nitro-Phenyl)-Ethylamino]-3,4-Dioxo-Cyclobut- 1-Enylamino}-Benzonitrile To the squarate of Example 1, step 1 (0.598 g, 2.47 mmol) in ethanol (50 mL) was added (R)-α-methyl-4-nitrobenzylamine hydrochloride (0.50 g, 2.5 mmol) and N,N-diisopropylethylamine (0.43 g, 2.5 mmol). The mixture was heated at reflux for 16 hours. After cooling the precipitate was filtered off to afford 0.70 g (78%) of product as an orange solid: mp 290°–295° C.; [α]$^{25}_D$–100.52 (DMSO); $^1$H NMR (DMSO-d$_6$): δ 9.98 (s, 1H), 8.32 (d, 1H), 8.25 (d, 2H), 7.79 (d, 2H), 7.68 (d, 2H), 7.57 (d, 2H), 5.42 (m, 1H), 1.61 (d, 3H). IR (KBr): 3200, 2220, 1790, 1670, 1600 cm$^{-1}$; MS (m/z) 362 (M$^+$).

Elemental analysis for $C_{19}H_{14}N_4O_4$ Calc'd: C, 62.98; H, 3.89; N, 15.46. Found: C, 62.38; H, 3.73; N, 14.95.

EXAMPLE 8

3-[3,4-Dioxo-2-((R)-1-Phenyl-Ethylamino)-Cyclobut-1-Enylamino] -Benzonitrile

Step 1)

Preparation of 3-(3,4-dioxo-2-ethoxy-cyclobut-1-enylamino)-benzonitrile

3-Aminobenzonitrile (2.06 g, 17.4 mmol) was added to a solution of 3,4-diethoxy- 3-cyclobutene-1,2-dione (2.97 g, 17.5 mmol) in absolute ethanol (50 mL). The mixture was heated at reflux overnight. The mixture was cooled and the resulting yellow precipitate was collected by vacuum filtration. Yield: 3.40 g (81%): $^1$H NMR (DMSO-d$_6$): δ 10.95 (s, 1H), 7.75–7.40 (m, 4H), 4.73 (q, 2H), 1.39 (t, 3H).

Step 2)

Preparation of 3-[3,4-dioxo-2-((R)-1-phenyl-ethylamino)-cyclobut- 1-enylamino]-benzonitrile To the above squarate (1.00 g, 4.13 mmol) in ethanol (100 mL) was added (R)-α-methylbenzylamine (0.53 mL, 4.1 mmol). The mixture was heated at reflux overnight and vacuum filtered. The precipitate was triturated twice with hot methanol to afford 0.80 g (61%) of product as a pale yellow solid: mp 289°–290° C. (dec); [α]$^{25}_D$–13.9 (DMSO); $^1$H NMR (DMSO-d$_6$): δ 9.72 (s, 1H), 8.25 (d, 1H), 7.90–7.28 (m, 9H), 5.30 (m, 1H), 1.60 (d, 3H). IR (KBr): 3200, 2220, 1790, 1650, 1600 cm$^{-1}$; MS (m/z) 317 (M$^+$).

Elemental analysis for $C_{19}H_{15}N_3O_2$ Calc'd: C, 71.91; H, 4.76; N, 13.24. Found: C, 71.80; H, 4.61; N, 13.33.

EXAMPLE 9

4-[3,4-Dioxo-2-(1-Methyl-1-Phenyl-Ethylamino)-Cyclobut- 1-Enylamino]-Benzonitrile To the squarate of Example 1, step 1 (0.81 g, 3.3 mmol) in ethanol (30 mL) was added α,α-dimethylbenzylamine (0.45 g, 3.3 mmol). The mixture was heated at reflux for 20 hours. After cooling the precipitate was filtered off and chromatographed ($CH_3OH/CH_2Cl_2$) to afford 0.41 g (37%) of product as yellow solid: mp>300° C.; $^1$H NMR (DMSO-$d_6$): δ 10.08 (s, 1H), 8.38 (s, 1H), 7.79 (d, 2H), 7.61 (d, 2H), 7.48–7.27 (m, 5H), 1.78 (s, 6H). IR (KBr): 3200, 2230, 1790, 1675, 1600 $cm^{-1}$; MS (m/z) 331 ($M^+$).

Elemental analysis for $C_{20}H_{17}N_3O_2$.(0.1 $CH_3OH$).(0.05 $CH_2Cl_2$) Calc'd: C, 71.43; H, 5.21; N, 12.40. Found: C, 71.30; H, 5.33; N, 12.69.

EXAMPLE 10

4-[3,4-Dioxo-2-((R)-1-Phenyl-Propylamino)-Cyclobut-1Enylamino-Benzonitrile

To the squarate of Example 1, step 1 (1.79 g, 7.39 mmol) in ethanol (30 mL) was added (R)-1-phenyl-propylamine (1.00 g, 7.40 mmol). The mixture was heated at reflux for 18 hours, cooled slightly and vacuum filtered to afford 1.76 g (72%) of product as a yellow solid: mp 242°–243° C.; $[\alpha]^{25}_D$–52.73 (DMSO); $^1$H NMR, (DMSO-$d_6$): δ 9.84 (s, 1H), 8.12 (br d, 1H), 7.76 (d, 2H), 7.56 (d, 2H), 7.42–7.27 (m, 5H), 5.06 (m, 1H), 1.94 (m, 2H), 0.90 (t, 3H). IR (KBr): 3200, 2220, 1790, 1670, 1600 $cm^{-1}$; MS (m/z) 331 ($M^+$).

Elemental analysis for $C_{20}H_{17}N_3O_2$ Calc'd: C, 72.49; H, 5.17; N, 12.68. Found: C, 72.42; H, 5.01; N, 12.73.

EXAMPLE 11

4-[3,4-Dioxo-2-((S)-1-Phenyl-Propylamino)-Cyclobut-1-Enylamino]-Benzonitrile

To the squarate of Example 1, step 1 (1.79 g, 7.39 mmol) in ethanol (30 mL) was added (S)-1-phenyl-propylamine (1.00 g, 7.40 mmol). The mixture was heated at reflux for 18 hours, cooled slightly and vacuum filtered to afford 1.61 g (66%) of product as a yellow solid: mp 241°–243° C.; $[\alpha]^{25}_D$+52.33 (DMSO); $^1$H NMR (DMSO-$d_6$): δ 9.84 (s, 1H), 8.21 (br d 1H), 7.76 (d, 2H) 7.56 (d, 2H), 7.42–7.27 (m, 5H), 5.06 (m, 1H), 1.94 (m, 2H), 0.90 (t, 3H). IR (KBr): 3200, 2220, 1790, 1670, 1600 $cm^{-1}$; MS (m/z) 331 ($M^+$).

Elemental analysis for $C_{20}H_{17}N_3O_2$ Calc'd: C, 72.49; H, 5.17; N, 12.68. Found: C, 72.17; H, 5.04; N, 12.80.

EXAMPLE 12

4-[3.4-Dioxo-2-(Benzylamino)-Cyclobut-1-Enylamino]-Benzonitrile

To the squarate of Example 1, step 1 (1.00 g, 4.13 mmol) in ethanol (30 mL) was added benzylamine (0.45 mL, 4.1 mmol). The mixture was heated at reflux for 18 hours, cooled slightly and vacuum filtered. The precipitate was triturated with hot methanol to afford 0.78 g (62%) of product as yellow solid: mp 288°–290° C. (dec); $^1$H NMR (DMSO-$d_6$): δ 9.91 (s, 1H), 8.10 (m, 1H), 7.79 (d, 2H), 7.75 (d, 2H), 7.55 (d, 2H),7.91–7.78(m, 5H),4.82(d, 2H). IR(KBr): 3190, 2220, 1790, 1660, 1575$cm^{-1}$; MS (m/z) 303 ($M^+$).

Elemental analysis for $C_{18}H_{13}N_3O_2$ Calc'd: C, 71.28; H, 4.32; N, 13.85. Found: C, 71.07; H, 4.16; N, 12.89.

EXAMPLE 13

(R)-4-{2-[1-(4-Methyl-Phenyl)-Ethylamino]-3,4-Dioxo-Cyclobut- 1-Enylamino}-Benzonitrile To the squarate of Example 1, step 1 (1.00 g, 4.13 mmol) in ethanol (30 mL) was added (R)-1-(p -tolyl)-ethylamine (0.56 g, 4.1 mmol). The mixture was heated at reflux for 18 hours, cooled slightly and vacuum filtered to afford 1.02 g (75%) of product as a yellow solid: mp>300° C.; $[\alpha]^{25}_D$–56.01 (DMSO); $^1$H NMR (DMSO-$d_6$): δ 9.81 (s, 1H), 8.10 (m, 1H), 7.76 (d, 2H), 7.5.5 (d, 2H), 7.29 (d, 2H), 7.19 (d, 2H), 5.26 (m, 1H), 1.57 (d, 3H). IR (KBr): 3200, 2220, 1790, 1670, 1600 $cm^{-1}$; MS (m/z) 331 ($M^+$).

Elemental analysis for $C_{20}H_{17}N_3O_2$ Calc'd: C, 72.49; H, 5.17; N, 12.68. Found: C, 72.42; H, 5.07; N, 12.82.

EXAMPLE 14

(R)-4-{2-[1-(4-Methoxy-Phenyl)-Ethylamino]-3,4-Dioxo-Cyclobut- 1-Enylamino}-Benzonitrile To a solution of (1R, 1'R)-N-(1'-phenylethyl)-1-(4"-methoxyphenyl)-ethylamine (1.37 g, 5.36 mmol; prepared as in *J. Med Chem.* 1992, 35, 2327) and ammonium formate (1.01 g, 16.0 mmol) in methanol (125 mL) was added 10% palladium on activated carbon. The suspension was refluxed for 2 h, filtered through Celite and concentrated. The squarate of Example 1, step 1 (1.00 g, 4.13 mmol) was added to a solution of the resulting residue in ethanol (30 mL). The mixture was heated at reflux for 18 h, cooled slightly and vacuum filtered. The precipitate was chromatographed ($CH_3OH/CH_2Cl_2$) and recrystallized ($CH_3OH/CH_2Cl_2$) to afford 0.21 g (15%) of product as a yellow solid: mp>300° C.; $[\alpha]^{25}_D$–46.95 (DMSO); $^1$H NMR (DMSO-$d_6$): δ 9.89 (s, 1H), 8.13 (d, 1H), 7.77 (d, 2H), 7.56 (d, 2H), 7.34 (d, 2H), 6.95 (d, 2H), 5.23 (m, 1H), 3.73 (s, 3H), 1.57 (d, 3H). IR (KBr): 3200, 2200, 1800, 1670, 1575 $cm^{-1}$; MS (m/z) 347 ($M^+$).

Elemental analysis for $C_{20}H_{17}N_3O_3$.(0.03 $CH_2Cl_2$) Calc'd: C, 68.75; H, 4.91; N, 12.01. Found: C, 68.40; H, 4.74; N, 11.89.

EXAMPLE 15

(R)-4-{3,4-Dioxo-2-[1-(4-Trifluoromethoxy-Phenyl)-Ethylamino]-Cyclobut- 1-Enylamino}-Benzonitrile To a solution of (1R, 1'R)-N-(1'-phenylethyl)-1-(4"-trifluoromethoxyphenyl)ethylamine (1.92 g, 6.21 mmol; prepared as in *J. Med. Chem.* 1992, 35, 2327) and ammonium formate (1.17 g, 18.6 mmol) in methanol (150 mL) was added 10% palladium on activated carbon. The suspension was refluxed for 2 h, filtered through Celite and concentrated. The squarate of Example 1, step 1 (1.00 g, 4.13 mmol) was added to a solution of the resulting residue in ethanol (35 mL). The mixture was heated at reflux for 18 h, cooled slightly and vacuum filtered. The precipitate was combined with a second crop of solid obtained from the cooled filtrate, chromatographed ($CH_3OH/CH_2Cl_2$) and recrystallized ($CH_3OH/CH_2Cl_2$) to afford 0.74 g (45%) of product as a white solid: mp 281°–284° C. (dec); $[\alpha]^{25}_D$–55.94 (DMSO); $^1$H NMR (DMSO-$d_6$): δ 9.94 (s, 1H), 8.22 (d, 1H), 7.78 (d, 2H), 7.60–7.51. (m, 4H), 7.40 (d, 2H), 5.33 (m, 1H), 1.60 (d, 3H). IR (KBr): 3200, 2200, 1800, 1670, 1560 $cm^{-1}$; MS (m/z) 401 ($M^+$).

Elemental analysis for $C_{20}H_{14}F_3N_3O_3$ Calc'd: C, 59.85; H, 3.52; N, 10.47. Found: C, 59.94; H, 3.38; N, 10.43.

EXAMPLE 16

4-[3,4-Dioxo-2-(2,2,2-Trifluoro-1-Phenyl-Ethylamino)-Cyclobut- 1-Enylamino]-Benzonitrile To a solution of N-2,2,2-trifluoro-1-phenylethyl-N-1'-(phenyl)ethylamine (1.65 g, 6.22 mmol; prepared as in *J. Org. Chem.* 1977, 42, 2436) and ammonium formate (1.17 g, 18.6 mmol) in methanol (150 mL) was added 10% palladium on activated carbon. The suspension was refluxed for 4 h, filtered through Celite and concentrated to a volume of approximately 10 mL. The squarate of Example 1, step 1 (1.00 g, 4.13 mmol) and ethanol (20 mL) were added and the mixture was heated at reflux for 18 h, cooled slightly and vacuum filtered to remove a small amount of solid. The filtrate was chromatographed ($CH_3OH/CH_2Cl_2$) and the resulting yellow solid crystallized from chloroform and ether to afford 0.72 g (47%) of product as a pale yellow solid: mp 206°–207° C.; $^1$H NMR (DMSO-$d_6$): δ 9.99 (s, 1H), 8.88 (d, 1H), 7.82 (d, 2H), 7.60–7.46 (m, 9H), 5.98 (m, 1H), 3.73 (s, 3H). IR (KBr): 3200 2200, 1800, 1690, 1570 cm$^{-1}$; MS (m/z) 371 (M$^+$).

Elemental analysis for $C_{19}H_{12}F_3N_3O_2$ Calc'd: C, 61.46; H, 3.26; N, 11.32. Found: C, 61.26; H, 3.16; N, 11.23.

EXAMPLE 17

(R)-4-[3,4-Dioxo-2-(Phenyl-Ethylamino)-Cyclobut-1-Enylamino]- 3-Methyl-Benzonitrile Step 1)

Preparation of 4-(3,4-Dioxo-2-ethoxy-cyclobut-1-enylamino)-3-methylbenzonitrile

4-Amino-3-methylbenzonitrile (1.94 g, 14.7 mmol) was added to a solution of 3,4-diethoxy-3-cyclobutene-1,2-dione (2.53 g, 14.9 mmol) in acetonitrile (5 mL). After refluxing the mixture for 24 h a second portion of 3,4-diethoxy-3-cyclobutene- 1,2-dione (1.15 g, 6.76 mmol) was added and heating was continued for an additional 48 h. The reaction mixture was diluted with ethyl acetate (50 mL), stirred vigorously and filtered free of undissolved solid. The filtrate was chromatographed ($CH_3OH/CH_2Cl_2$) to afford 0.90 g (24%) of product as a yellow solid: $^1$H NMR (DMSO-$d_6$): δ 10.50 (s, 1H), 7.76–7.63 (m, 2H), 7.31 (d, 1H), 4.71 (q, 2H), 2.33 (s, 3H), 1.38 (t, 3H).

Step 2)

Preparation of (R)-4-[3,4-Dioxo-2-(1-phenyl-ethylamino)-cyclobut-1-enylamino]-3-methyl-benzonitrile To the above squarate (0.90 g, 3.51 mmol) in ethanol (40 mL) was added (R)-α-methylbenzylamine (0.45 mL, 3.49 mmol). The mixture was heated at reflux for 18 h. The resulting clear solution solution was concentrated and the residue chromatographed ($CH_3OH/CH_2Cl_2$) to afford 0.98 g (85%) of product as a yellow solid: mp 110°–130° C. (dec); $[α]^{25}_D$–40.91 (DMSO) $^1$H NMR (DMSO-$d_6$): δ 8.95 (s, 1H), 8.58 (d, 2H), 7.70–7.28 (m, 8H), 5.36 (m, 1H), 2.33 (s, 3H), 1.61 (d, 3H), IR (KBr): 3250, 2220, 1790, 1690, 1590 cm$^{-1}$; MS (m/z) 332 (MH$^+$).

Elemental analysis for $C_{20}H_{17}N_3O_2$.(0.10 $CH_2Cl_2$) Calc'd: C, 71.03; H, 5.10; N, 12.36. Found: C, 71.37; H, 5.09; N, 12.61.

EXAMPLE 18

(R)-4-[3,4-Dioxo-2-(Phenyl-Ethylamino)-Cyclobut-1-Enylamino]- 3-Ethyl-Benzonitrile Step 1)

Preparation of 4-(3,4-Dioxo-2-ethoxy-cyclobut-1-enylamino)-3-ethyl-benzonitrile

4-Amino-3-ethylbenzonitrile (2.00 g, 13.7 mmol) was added to a solution of 3,4-diethoxy-3-cyclobutene-1,2-dione (2.30 g, 13.5 mmol) in acetonitrile (5 mL). After refluxing the mixture for 24 h a second portion of 3,4-diethoxy-3-cyclobutene- 1,2-dione (1.15 g, 6.76 mmol) was added and heating was continued for an additional 24 h. The reaction mixture was diluted with ethyl acetate (45 mL), stirred vigorously and filtered free of undissolved solid. The filtrate was concentrated and the resulting residue was purified by chromatographed ($CH_3OH/CH_2Cl_2$) and trituration with ether to afford 0.86 g (24%) of product as a light yellow solid: $^1$H NMR (DMSO-$d_6$): δ 10.57 (s, 1H), 7.77–7.66 (m, 2H), 7.31 (d, 1H), 4.71 (q, 2H), 2.73 (q, 2H), 1.37 (t, 3H), 1.13 (t, 3H).

Step 2)

Preparation of (R)-4-[3,4-Dioxo-2-(1-phenyl-ethylamino)-cyclobut-1-enylamino] -3-ethyl-benzonitrile To the above squarate (0.85 g, 3.14 mmol) in ethanol (25 mL) was added (R)-α-methylbenzylamine (0.41 mL, 3.18 mmol). The mixture was heated at reflux for 18 h, cooled slightly and suction filtered. The filtrate was cooled by gradual evaporation of solvent and the precipitate which formed was collected in two crops to afford 0.76 g (70%) of product as an off-white solid: mp 206°–207° C. (dec); $[α]^{25}_D$ –45.25 (DMSO); $^1$H NMR (DMSO-$d_6$): δ 9.98 (s, 1H), 8.55 (d, 2H), 7.68–7.29 (m, 8H), 5.37 (m, 1H), 2.69 (q, 2H), 1.61 (d, 3H), 1.20 (t, 3H). IR (KBr): 3200, 2200, 1800, 1670, 1570 cm$^{-1}$; MS (m/z) 345 (M$^+$).

Elemental analysis for $C_{21}H_{19}N_3O_2$ Calc'd: C, 73.03; H, 5.54; N, 12.17. Found: C, 72.69; H, 5.52; N, 12.18.

EXAMPLE 19

(R)-N-(4-Cyano-Phenyl)-N-[3,4-Dioxo-2-(1-Phenyl-Ethylamino)-Cyclobut- 1-Enyl-Acetamide To a stirred solution of the squarate of Example 1, step 2 (1.77 g, 5.58 mmol) in N,N-dimethylformamide (50 mL) was added, in one portion, sodium hydride (as a 60% dispersion in mineral oil; 0.252 g, 6.30 mmol). The frothy suspension was stirred at rt for 15 min and then at 0° C. for an additional 1 h. Acetic anhydride (0.58 mL, 6.15 mmol) was added and the reaction mixture was stirred at 0° C. for 1.5 h and then allowed to warm to rt. After an additional 1 h of stirring the reaction solution was concentrated. The resulting yellow solid was washed with successive portions of acetone, methylene chloride and ethyl acetate. The combined washings were concentrated and the resulting residue chromatographed to afford 0.48 g (24%) of product as an off-white solid: mp 240°–243° C.; $[α]^{25}_D$–94.66 (DMSO); $^1$H NMR (DMSO-$d_6$): δ 8.29 (d, 1H), 7.96 (d, 2H), 7.69 (d, 2H), 7.45–7.25 (m, 5H), 5.49 (m, 1H), 2.06 (s, 3H), 1.59 (d, 3H). IR (KBr): 3340, 2230, 1800, 1740, 1690, 1610 cm$^{-1}$; MS (m/z) 359 (M$^+$).

Elemental analysis for $C_{21}H_{17}N_3O_3$.(0.05 $CH_2Cl_2$) Calc'd: C, 69.53; H, 4.74; N 11.56. Found: C, 69.16; H, 4.74; N, 11.53.

Smooth muscle relaxing activity of the compounds of this invention was established in accordance with standard pharmaceutically accepted test procedures in representative compounds as follows:

Sprague-Dawley rats (150–200 g) are rendered unconscious by $CO_2$ asphyxiation and then euthanized by cervical dislocation. The bladder is removed into warm (37 deg. C) physiological salt solution (PSS) of the following composition (mM): NaCl, 118.4; KCl, 4.7; $CaCl_2$, 2.5; $MgSO_4$, 4.7; $H_2O$, 1.2; $NaHCO_3$, 24.9; $KH_2PO_4$, 1.2; glucose, 11.1; EDTA, 0.023; gassed with 95% $O_2$; 2/5% $CO_2$; pH 7.4. The bladder is opened and then cut into strips 1–2 mm in width and 7–10 mm in length. The strips are subsequently suspended in a 10 mL tissue bath under an initial resting tension of 1.5 g. The strips are held in place by two surgical clips one of which is attached to fixed hook while the other is attached to an isometric force transducer. The preparations, which usually exhibit small spontaneous contractions, are allowed to recover for a period of 1 hour prior to a challenge with 0.1 µM carbachol. The carbachol is then washed out and the tissue allowed to relax to its resting level of activity. Following 1 further 30 min period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremenlal increases in the concentration of test compound or vehicle are introduced into the tissue bath. Contractile activity is measured for each compound or vehicle concentration during the last min of a 30 min challenge.

Isometric force developed by the bladder strips is measured using a concentration required to elicit 50% inhibition of pre-drug contractile activity ($IC_{50}$ concentration) is calculated from this concentration-response curve. The maximum percentage inhibition of contractile activity evoked by a test compound is also recorded for concentrations of test compound<or equal to 30 µM.

The results of this study are shown in Table I.

TABLE I

Inhibition of Contractions in Isolated Rat Bladder Strips

| Compound | n | $IC_{50}$ | Inhibition of Force (%) at (x) µM |
|---|---|---|---|
| Example 1 | 6 | 0.056 µM | — |
| Example 4 | 3 | 2.3 µM | — |
| Example 5 | 3 | — | 38% (30 µM) |
| Example 9 | 4 | — | 22% (30 µM) |
| Example 11 | 4 | — | 28% (30 µM) |

Hence, the compounds of this invention have a pronounced effect on smooth muscle contractility and are useful in the treatment of urinary incontinence, irritable bladder and bowel disease, asthma, hypertension, stroke, and similar diseases as mentioned above, which are amenable to treatment with potassium channel activating compounds by administration, orally, parenterally, or by aspiration to a patient in need thereof.

What is claimed is:

1. A compound of the formula:

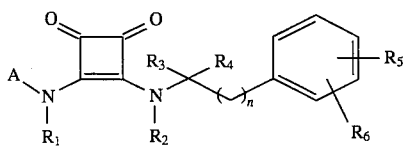

(I)

wherein:

$R_1$ is hydrogen, $C_{1-10}$ straight or branched chain alkyl, $C_{3-10}$ cyclic or bicyclic alkyl, alkanoyl of 2 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

$R_2$ is hydrogen, $C_{1-10}$ straight or branched chain alkyl or $C_{3-10}$ cyclic or bicyclic alkyl;

A is selected from the following:

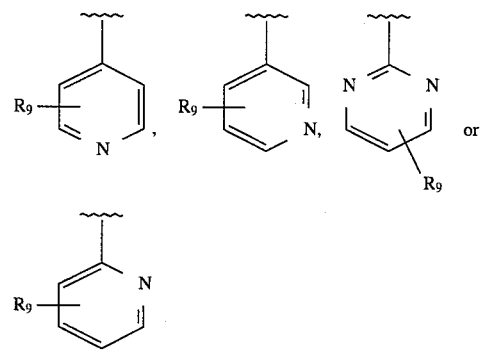

wherein:

$R_9$ is hydrogen, $C_{1-6}$ alkyl, $C_{1-6}$ perfluoroalkyl, $C_{1-6}$ alkoxy, $C_{1-6}$ perfluoroalkoxy, amino, $C_{1-12}$ mono-or dialkylamino, $C_{1-6}$ alkylsulfonamido, $C_{1-6}$ alkylcarboxamido, nitro, cyano, carboxyl, chloro, bromo, fluoro, iodo;

n is an integer from 0 to 6;

$R_3$ and $R_4$ are, independent from each other, hydrogen, $C_{1-10}$ straight or branched chain alkyl, or $C_{3-10}$ cyclic or bicyclic alkyl; $C_{1-10}$ perfluoro alkyl, $C_{1-10}$ hydroxyalkyl, $C_{1-10}$ alkoxyalkyl, fluoro; or, when taken together, form a spirocyclic ring containing a total of 3–7 carbon atoms;

$R_5$ and $R_6$, independent from each other, are selected from the following: cyano, nitro, $C_{1-6}$ alkyl, $C_{1-6}$ perfluoroalkyl, $C_{1-6}$ alkoxy, $C_{1-6}$ perfluoroalkoxy, amino, $C_{1-12}$ mono- or dialkylamino, sulfonamide, $C_{1-6}$ alkylsulfonamido, $C_{6-12}$ arylsulfonamido, $C_{1-6}$ alkylcarboxamido, $C_{6-12}$ arylcarboxamido, $C_{1-6}$ alkylsulfonyl, $C_{1-6}$ perfluoroalkylsulfonyl, $C_{6-12}$ arylsulfonyl, chloro, bromo, fluoro, iodo, 1-imidazolyl, carboxyl, carboalkoxy, hydroxyl, or hydrogen;

or a pharmaceutically acceptable salt thereof.

2. A compound of claim 1, in which A is selected from the following:

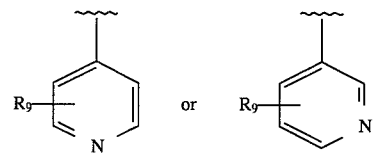

wherein:

n=0;

$R_3$ and $R_4$ are, independent from each other, hydrogen, $C_{1-10}$ straight or branched chain alkyl, $C_{1-10}$ perfluoro alkyl, $C_{1-10}$ hydroxyalkyl or fluoro;

$R_5$ and $R_6$, independent from each other, are selected from the following: cyano, nitro, $C_{1-6}$ alkyl, $C_{1-6}$ perfluoroalkyl, $C_{1-6}$ alkoxy, $C_{1-6}$ perfluoroalkoxy, amino, chloro, bromo, fluoro, iodo, carboxyl, carboalkoxy, hydroxyl, hydrogen;

or a pharmaceutically acceptable salt thereof.

3. A method for reducing the adverse effects of smooth muscle contractions which comprises administering, orally or parenterally, to a patient in need thereof, a compound of the formula:

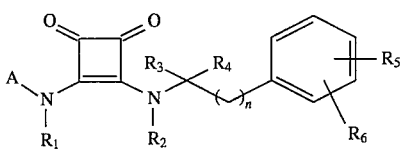

wherein:

$R_1$ is hydrogen, $C_{1-10}$ straight or branched chain alkyl, $C_{3-10}$ cyclic or bicyclic alkyl, alkanoyl of 2 to 7 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms;

$R_2$ is hydrogen, $C_{1-10}$ straight or branched chain alkyl or $C_{3-10}$ cyclic or bicyclic alkyl;

A is selected from the following:

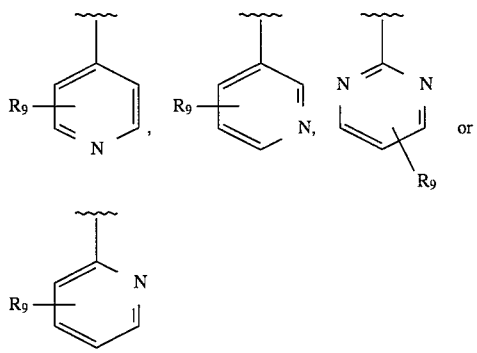

wherein:

$R_9$ is hydrogen, $C_{1-6}$ alkyl, $C_{1-6}$ perfluoroalkyl, $C_{1-6}$ alkoxy, $C_{1-6}$ perfluoroalkoxy, amino, $C_{1-12}$ mono-or dialkylamino, $C_{1-6}$ alkylsulfonamido, $C_{1-6}$ alkylcarboxamido, nitro, cyano, carboxyl, chloro, bromo, fluoro, iodo;

n is an integer from 0 to 6;

$R_3$ and $R_4$ are, independent from each other, hydrogen, $C_{1-10}$ straight or branched chain alkyl, or $C_{3-10}$ cyclic or bicyclic alkyl; $C_{1-10}$ perfluoro alkyl, $C_{1-10}$ hydroxyalkyl, $C_{1-10}$ alkoxyalkyl, fluoro; or, when taken together, form a spirocyclic ring containing a total of 3–7 carbon atoms;

$R_5$ and $R_6$, independent from each other, are selected from the following: cyano, nitro, $C_{1-6}$ alkyl, $C_{1-6}$ perfluoroalkyl, $C_{1-6}$ alkoxy, $C_{1-6}$ perfluoroalkoxy, amino, $C_{1-12}$ mono-or dialkylamino, sulfonamide, $C_{1-6}$ alkylsulfonamido, $C_{6-12}$ arylsulfonamido, $C_{1-6}$ alkylcarboxamido, $C_{6-12}$ arylcarboxamido, $C_{1-6}$ alkylsulfonyl, $C_{1-6}$ perfluoroalkylsulfonyl, $C_{6-12}$ arylsulfonyl, chloro, bromo, fluoro, iodo, 1-imidazolyl, carboxyl, carboalkoxy, hydroxyl, or hydrogen;

or a pharmaceutically acceptable salt thereof.

4. The compound of claim 1 which is 3-(5-bromo-pyridin-3-ylamino)-4-(1-phenyl-ethylamino)-cyclobut- 3-ene-1,2-dione.

5. The compound of claim 1 which is 3-(1-phenyl-ethylamino)-4-(pyridin-4-ylamino)-cyclobut- 3-ene-1,2-dione.

6. The method of claim 2 in which the smooth muscle adversely contracting causes urinary incontinence.

7. The method of claim 2 in which the smooth muscle adversely contracting causes irritable bowel syndrome.

* * * * *